US010239809B2

(12) United States Patent
Faler et al.

(10) Patent No.: US 10,239,809 B2
(45) Date of Patent: Mar. 26, 2019

(54) METHODS FOR PREPARING BRIDGED BI-AROMATIC LIGANDS

(71) Applicant: Univation Technologies, LLC, Houston, TX (US)

(72) Inventors: Catherine Anne Faler, Houston, TX (US); C. Jeff Harlan, Houston, TX (US); Kevin P. Ramirez, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 15/568,115

(22) PCT Filed: Apr. 19, 2016

(86) PCT No.: PCT/US2016/028300
§ 371 (c)(1),
(2) Date: Oct. 20, 2017

(87) PCT Pub. No.: WO2016/172114
PCT Pub. Date: Oct. 27, 2016

(65) Prior Publication Data
US 2018/0079704 A1    Mar. 22, 2018

Related U.S. Application Data

(60) Provisional application No. 62/150,134, filed on Apr. 20, 2015.

(51) Int. Cl.
*C07C 41/26*    (2006.01)
*C07C 43/23*    (2006.01)
*C07D 311/82*    (2006.01)
*C07D 209/82*    (2006.01)
*C07D 213/32*    (2006.01)

(52) U.S. Cl.
CPC .............. *C07C 41/26* (2013.01); *C07C 43/23* (2013.01); *C07D 209/82* (2013.01); *C07D 213/32* (2013.01); *C07D 311/82* (2013.01)

(58) Field of Classification Search
CPC ................................ C07C 41/26; C07C 43/23
See application file for complete search history.

(56) References Cited

U.S. PATENT DOCUMENTS

2008/0269470 A1    10/2008    Boussie et al.
2013/0090438 A1    4/2013    Robert et al.

FOREIGN PATENT DOCUMENTS

WO    2005108406    11/2005

OTHER PUBLICATIONS

International Search Report & Written Opinion for related PCT Application PCT/US2016/028300, dated Jun. 23, 2016 (11 pgs).
International Preliminary Report on Patentability for related PCT Application PCT/US2016/028300, dated Nov. 2, 2017 (8 pgs).

*Primary Examiner* — Rosalynd A Keys
(74) *Attorney, Agent, or Firm* — Brooks, Cameron & Huebsch, PLLC

(57) ABSTRACT

New methods of preparing bridged bi-aromatic ligands are disclosed. The methods employ direct di-ortho-lithiation of aromatic rings of bridged protected bi-aromatic diphenols. The ligands may be used to prepare transition metal compounds useful as catalysts in olefin polymerization.

18 Claims, 3 Drawing Sheets

(1)

(2)

(4)

(6)

(7)

(9)

METHODS FOR PREPARING BRIDGED BI-AROMATIC LIGANDS

This application is a National Stage Application under 35 U.S.C. § 371 of International Application Number PCT/US2016/028300, filed Apr. 19, 2016 and published as WO 2016/172114 on Oct. 27, 2016, which claims the benefit to U.S. Provisional Application 62/150,134, filed Apr. 20, 2015, the entire contents of which are incorporated herein by reference in its entirety.

FIELD

The present disclosure is directed to improved methods for preparing bridged bi-aromatic ligands which are useful in the synthesis of transition metal olefin polymerization catalysts.

BACKGROUND

A major focus of the polyolefin industry in recent years has been on the development of new catalysts that deliver new and improved products. Bulky ligand transition metal compounds, for example, are now widely utilized in catalyst compositions to produce polyolefin polymers, such as polyethylene polymers.

WO 03/09162 discloses bridged bi-aromatic ligands, methods for their preparation, transition metal compounds derived therefrom and catalysts for olefin polymerization. However, the methods disclosed to synthesize the ligands involve many reaction steps and are therefore time consuming. This increases the cost of producing the ligands and negatively impacts the economics of catalyst manufacture.

Therefore, it would be desirable to provide new routes to bridged bi-aromatic ligands that contain fewer steps and that are simpler to perform.

SUMMARY

In one aspect there is provided a method for preparing a bridged bi-aromatic phenol ligand of formula (I) comprising at least one step of directly di-ortho-lithiating aromatic rings of a bridged protected bi-aromatic diphenol.

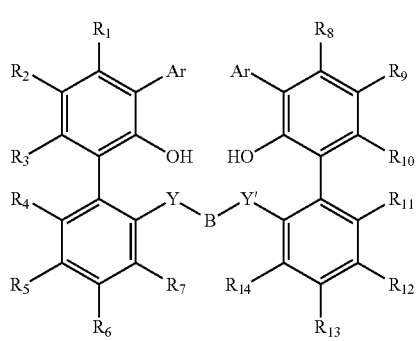

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; B is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or heteroaryl.

By "directly di-ortho-lithiating aromatic rings of a bridged protected bi-aromatic diphenol" it is meant that unsubstituted positions in aromatic rings ortho- to protected phenols may be lithiated in a single step and without the need for an intermediate, such as a halogenated intermediate.

The method may also comprise at least one step of aryl coupling. The method may comprise at least one step of Negishi coupling.

The method may comprise the following steps:

a) treating a protected bi-aromatic phenol of formula (II) with a lithiating agent to yield a dilithio protected bi-aromatic phenol of formula (III);

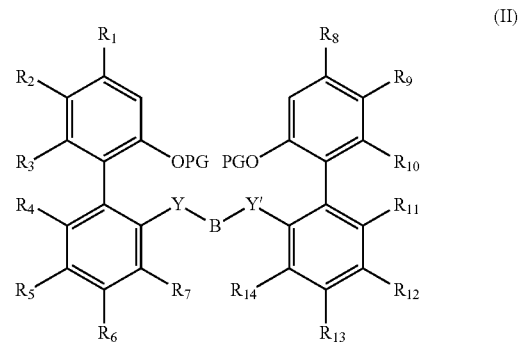

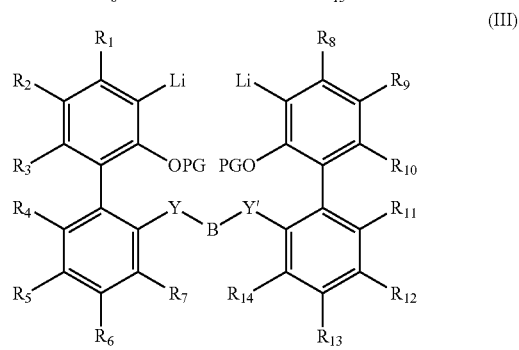

b) treating the dilithio protected bi-aromatic phenol of formula (III) with a zinc compound and a compound of formula ArX in the presence of a palladium or nickel catalyst, to yield a protected bi-aromatic phenol of formula (IV); and

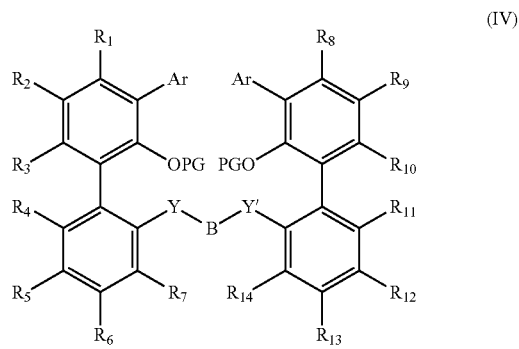

c) deprotecting the compound of formula (IV) to yield the bi-aromatic phenol ligand of formula (I);
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; B is a bridging group having from one to 50 non-hydrogen atoms; Y and Y' are independently selected from O, S, $NR^a$ and $PR^a$ wherein IV is optionally substituted hydrocarbyl; Ar is optionally substituted aryl or heteroaryl; X is halide; PG is a protecting group.

The method may comprise the steps of:
a) treating the dilithio protected bi-aromatic phenol of formula (III) with a zinc halide to yield a zinc halide salt of the protected bi-aromatic phenol of formula (V); and

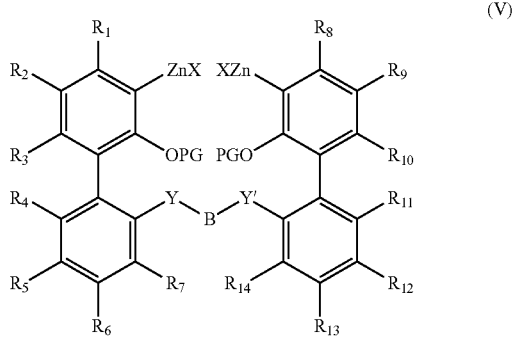

(V)

b) treating the zinc halide salt of the protected bi-aromatic phenol of formula (V) with a compound of formula ArX in the presence of a palladium or nickel catalyst to yield a compound of formula (IV).

In any one of the hereinbefore disclosed embodiments each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride, halide, optionally substituted alkyl, heteroalkyl, aryl, heteroaryl, alkoxyl, aryloxyl, silyl, dialkylamino, alkylthio and arylthio.

In any one of the hereinbefore disclosed embodiments each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride, and optionally substituted alkyl and aryl.

In any one of the hereinbefore disclosed embodiments the bridging group B may be selected from the group consisting of optionally substituted divalent hydrocarbyl and divalent heteroatom containing hydrocarbyl.

In any one of the hereinbefore disclosed embodiments the bridging group B may be selected from the group consisting of optionally substituted divalent alkyl, alkenyl, alkynyl, heteroalkyl, heteroalkenyl, heteroalkynyl, aryl, heteroaryl and silyl.

In any one of the hereinbefore disclosed embodiments the bridging group B may be represented by the general formula $-(QR^{15}_{2-z''})_{z'}-$ wherein each Q is either carbon or silicon and each $R^{15}$ may be the same or different from the others such that each $R^{15}$ is selected from the group consisting of hydride and optionally substituted hydrocarbyl and heteroatom containing hydrocarbyl, and optionally two or more $R^{15}$ groups may be joined into a ring structure having from 3 to 50 atoms in the ring structure not counting hydrogen atoms; z' is an integer from 1 to 10; and z" is 0, 1 or 2.

A major advantage of the herein disclosed methods is that the number of reaction steps may be reduced relative to known methods for preparing bridged bi-aromatic ligands.

A further advantage of the herein disclosed methods is the use of direct and selective di-ortho lithiation of the aromatic rings of a protected phenol.

In any one of the hereinbefore disclosed embodiments Ar may be optionally substituted phenyl, naphthyl, biphenyl, anthracenyl, and phenanthrenyl.

In any one of the hereinbefore disclosed embodiments Ar may be thiophene, pyridine, isoxazole, pyrazole, pyrrole, furan or benzo-fused analogues of these rings.

In any one of the hereinbefore disclosed embodiments the protecting group PG may be a protecting group including, but not limited to, methyl (Me), benzyl (Bn), substituted benzyl, for example, 2-methoxyphenylmethyl (MPM), alkoxymethyl, for example, methoxymethyl (MOM), tetrahydropyranyl (THP), silyl, for example, trimethylsilyl (TMS) or tert-butyldimethylsilyl (TBS) and allyl (Allyl). PG may be tetrahydropyranyl (THP).

In any one of the hereinbefore disclosed embodiments lithiation may be performed with an alkyl or aryl lithium compound.

In any one of the hereinbefore disclosed embodiments any one of the disclosed lithium containing compounds may have one or more of its lithium atoms coordinated with one or more Lewis bases. The Lewis bases may be an ether or a cyclic ether.

In any one of the hereinbefore disclosed embodiments the zinc compound may be a zinc halide or a zinc alkyl.

In any one of the hereinbefore disclosed embodiments the zinc halide may be zinc (II) chloride.

In any one of the hereinbefore disclosed embodiments the palladium catalyst may be a palladium phosphine catalyst. The palladium catalyst may comprise, for example, bis(tri-tert-butylphosphine)palladium, tetrakis(triphenylphosphine) palladium(0) (Pd(PPh$_3$)$_4$), bis[1,2-bis(diphenylphosphino) ethane]palladium(0) (Pd(dppe)$_2$), 1,1'-bis (diphenylphosphino)ferrocene palladium (Pd(dppf)), and (2,2'-bis(diphenylphosphino)-1,1'-binaphthyl palladium (Pd (BINAP).

In any one of the hereinbefore disclosed embodiments the palladium phosphine catalyst may be bis(tri-tert-butylphosphine)palladium.

In any one of the hereinbefore disclosed embodiments the protecting group PG may be a protecting group including, but not limited to: methyl (Me), benzyl (Bn), substituted benzyl, for example, 2-methoxyphenylmethyl (MPM), alkoxymethyl, for example, methoxymethyl (MOM), tetrahydropyranyl (THP), silyl, for example, trimethylsilyl (TMS) or tert-butyldimethylsilyl (TBS) and allyl (Allyl). PG may be tetrahydropyranyl (THP) or methoxymethyl.

In any one of the hereinbefore disclosed embodiments deprotection may comprise treatment with acid. The acid may be any protic acid. Exemplary acids include hydrochloric acid or p-toluene sulfonic acid.

The herein disclosed methods may comprise any combination of the above disclosed embodiments.

In any one of the hereinbefore disclosed embodiments the ligand of formula (I) may have formula (XIV)

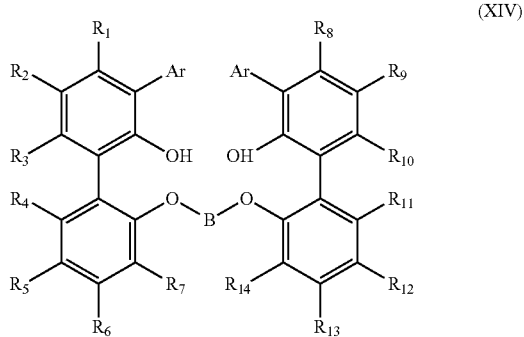

(XIV)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, Ar and B are as hereinbefore defined.

In another aspect there is provided a ligand of formula (I) or formula (XIV) prepared by any one of the hereinbefore disclosed methods.

DETAILED DESCRIPTION

Figure 1:
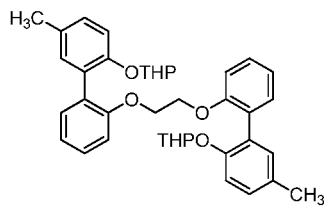
FIG. 1 depicts the chemical structures of exemplary compounds in accordance with this disclosure.
Figure 1:
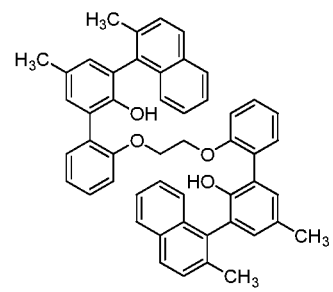
Figure 1:
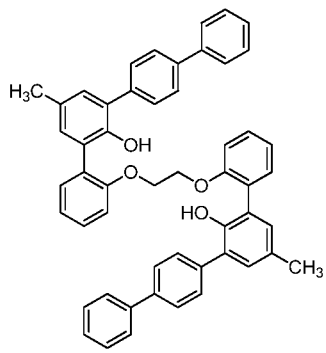
Figure 1:
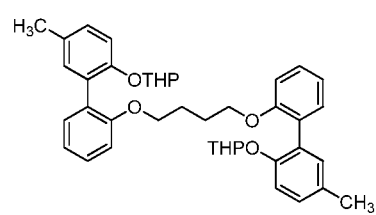
Figure 1:
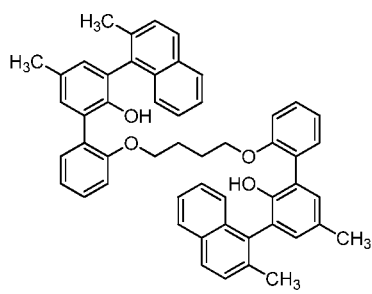
Figure 1:
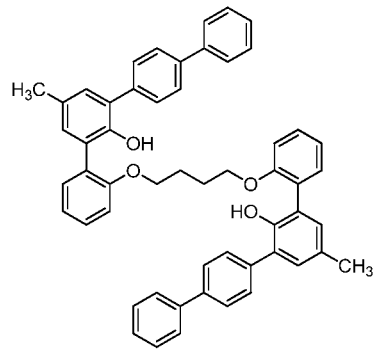

Before the present compounds, components, compositions, and/or methods are disclosed and described, it is to be understood that unless otherwise indicated this invention is not limited to specific compounds, components, compositions, reactants, reaction conditions, ligands, metallocene structures, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified. Thus, for example, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

Disclosed herein are methods for preparing bridged bi-aromatic ligands which are advantageous in comparison to known preparation methods. The disclosed methods make use of direct and selective di-ortho lithiation of protected phenols which greatly reduces the number of required reaction steps. The ligands find use in the preparation of transition metal compounds useful as catalysts in olefin polymerization.

The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, iso-butyl, t-butyl, octyl, decyl, and the like, as well as cycloalkyl groups such as cyclopentyl, cyclohexyl and the like. Generally, although again not necessarily, alkyl groups herein may contain 1 to about 12 carbon atoms. The term "lower alkyl" intends an alkyl group of one to six carbon atoms, specifically one to four carbon atoms. "Substituted alkyl" refers to alkyl substituted with one or more substituent groups (e.g., benzyl or chloromethyl), and the terms "heteroatom-containing alkyl" and "heteroalkyl" refer to alkyl in which at least one carbon atom is replaced with a heteroatom (e.g., —$CH_2OCH_3$ is an example of a heteroalkyl).

The term "alkenyl" as used herein refers to a branched or unbranched hydrocarbon group typically although not necessarily containing 2 to about 50 carbon atoms and at least one double bond, such as ethenyl, n-propenyl, iso-propenyl, n-butenyl, iso-butenyl, octenyl, decenyl, and the like. Generally, although again not necessarily, alkenyl groups herein contain 2 to about 12 carbon atoms. The term "lower alkenyl" refers to an alkenyl group of two to six carbon atoms, specifically two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 50 carbon atoms and at least one triple bond, such as ethynyl, n-propynyl, iso-propynyl, n-butynyl, isobutynyl, octynyl, decynyl, and the like. Generally, although again not necessarily, alkynyl groups herein may have 2 to about 12 carbon atoms. The term "lower alkynyl" refers to an alkynyl group of two to six carbon atoms, specifically three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group refers to an alkoxy group having one to six, more specifically one to four, carbon atoms. The term "aryloxy" is used in a similar fashion, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. A "lower alkyl thio" group refers to an alkyl thio group having one to six, more specifically one to four, carbon atoms. The term "arylthio" is used similarly, with aryl as defined below. The term "thioxy" refers to —SH.

The term "allenyl" is used herein in the conventional sense to refer to a molecular segment having the structure —CH=C=CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. The aryl substituents may have 1 to about 200 carbon atoms, typically 1 to about 50 carbon atoms, and specifically 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom (e.g., rings such as thiophene, pyridine, isoxazole, pyrazole, pyrrole, furan, etc. or benzo-fused analogues of these rings are included in the term "heteroaryl"). In some embodiments herein, multi-ring moieties are substituents and in such an embodiment the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus, boron or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to hydrocarbyl radicals containing 1 to about 50 carbon atoms, specifically 1 to about 24 carbon atoms, most specifically 1 to about 16 carbon atoms, including branched or unbranched, saturated or unsaturated species, such as alkyl groups, alkenyl groups, aryl groups, and the like. The term "lower hydrocarbyl" refers to a hydrocarbyl group of one to six carbon atoms, specifically one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," "substituted alkenyl" and the like, as alluded to in some of the aforementioned definitions, is meant that in the hydrocarbyl, hydrocarbylene, alkyl, alkenyl, aryl or other moiety, at least one hydrogen atom bound to a carbon atom is replaced with one or more substituents that are functional groups such as hydroxyl, alkoxy, alkylthio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds. The term "aromatic" is used in its usual sense, including unsaturation that is essentially delocalized across multiple bonds, such as around a ring.'

As used herein the term "silyl" refers to the —SiZ$^1$Z$^2$Z$^3$ radical, where each of Z$^1$, Z$^2$, and Z$^3$ is independently selected from the group consisting of hydride and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the —BZ$^1$Z$^2$ group, where each of Z$^1$ and Z$^2$ is as defined above.

As used herein, the term "phosphino" refers to the group —PZ$^1$Z$^2$, where each of Z$^1$ and Z$^2$ is as defined above. As used herein, the term "phosphine" refers to the group PZ$^1$Z$^2$Z$^3$, where each of Z$^1$, Z$^2$ and Z$^3$ is as defined above. The term "amino" is used herein to refer to the group —NZ$^1$Z$^2$, where each of Z$^1$ and Z$^2$ is as defined above. The term "amine" is used herein to refer to the group NZ$^1$Z$^2$Z$^3$, where each of Z$^1$, Z$^2$ and Z$^3$ is as defined above.

The term "saturated" refers to lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, acetylide, oxazolinyl, cyclohexenyl, acetyl and the like.

Other abbreviations used herein include: "iPr" to refer to isopropyl; "tBu" to refer to tertbutyl; "Me" to refer to methyl; "Et" to refer to ethyl; and "Ph" refers to phenyl.

Specific ligands which may be prepared by the methods disclosed herein include:
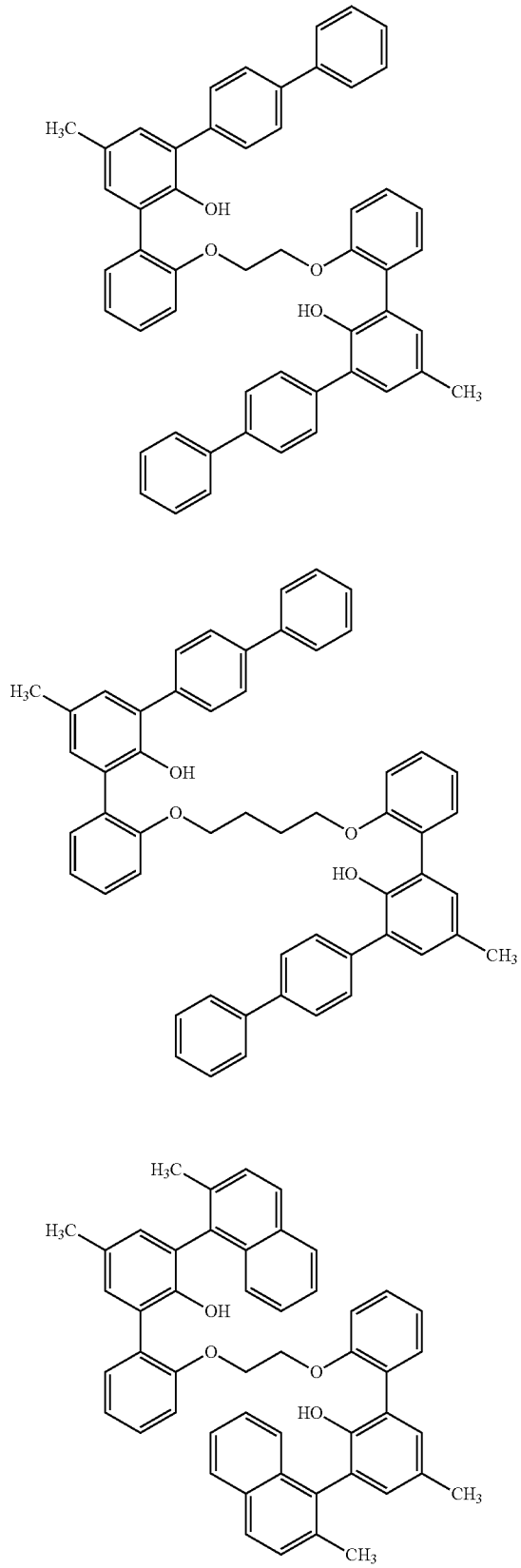
-continued
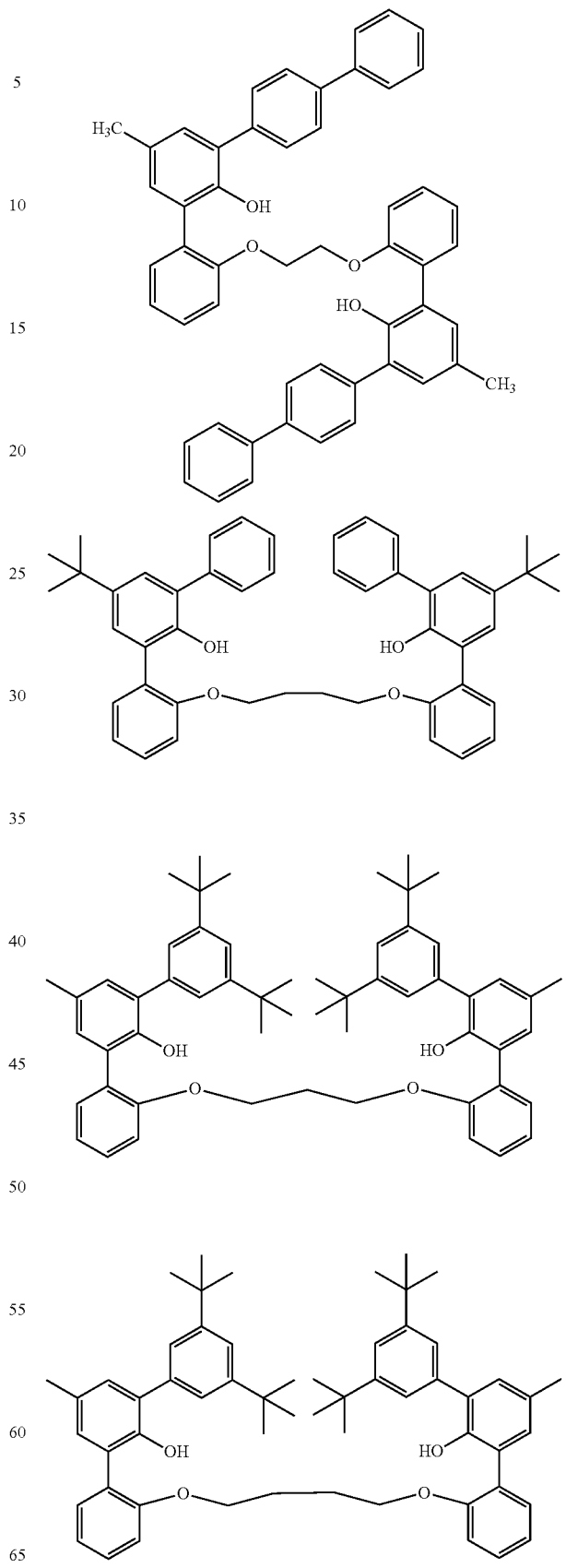

-continued
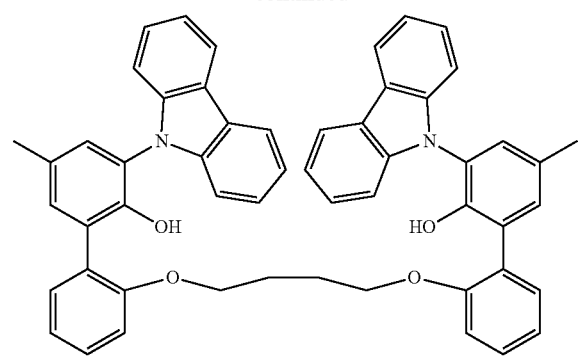
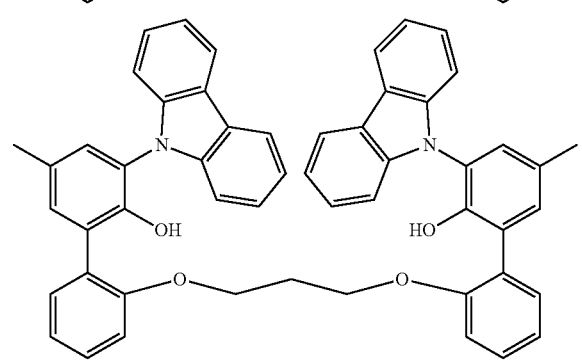
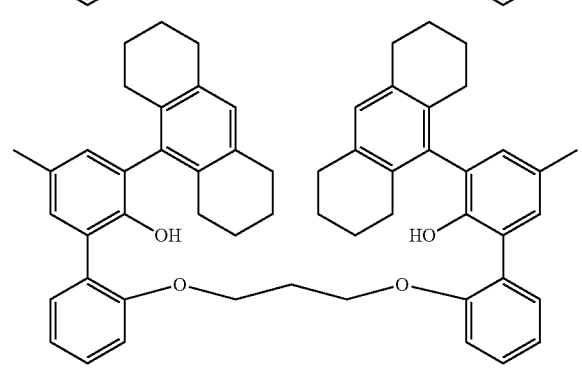
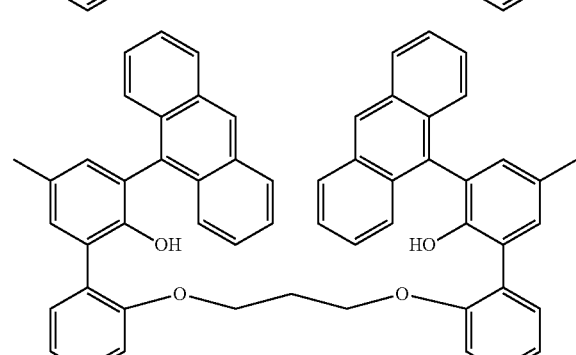
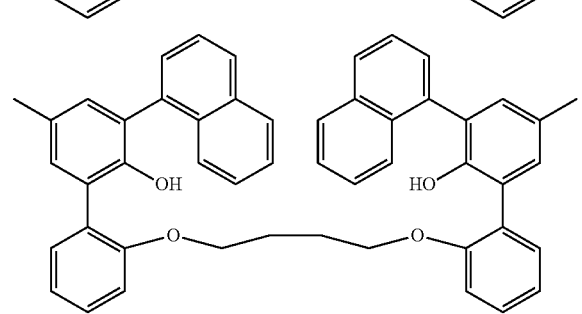
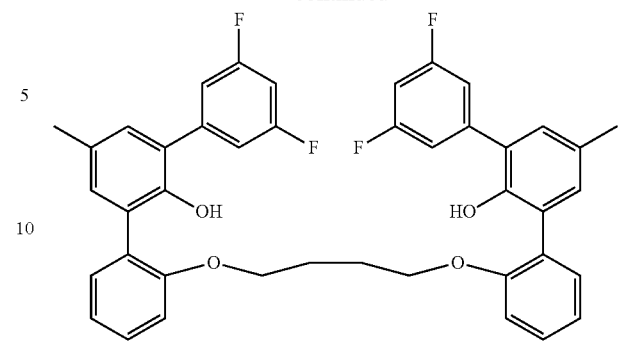
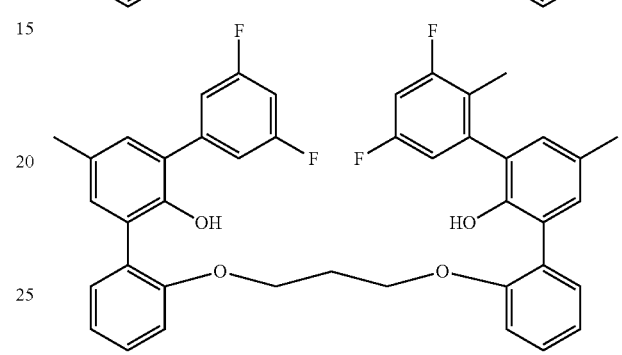
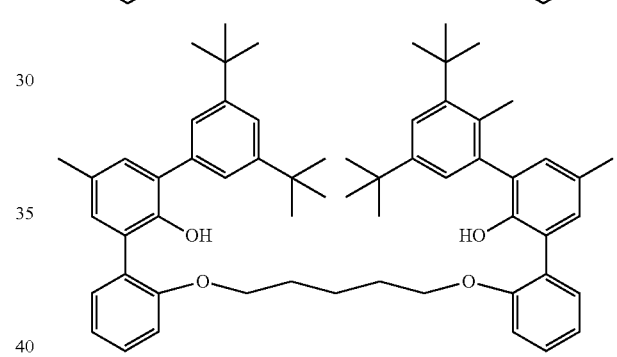
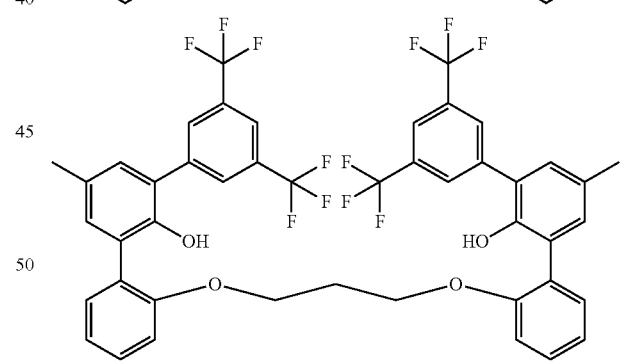
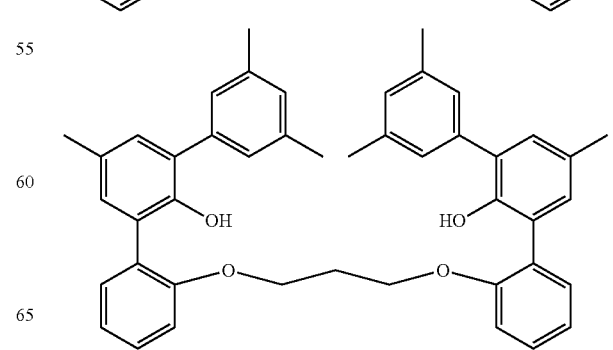

13
-continued
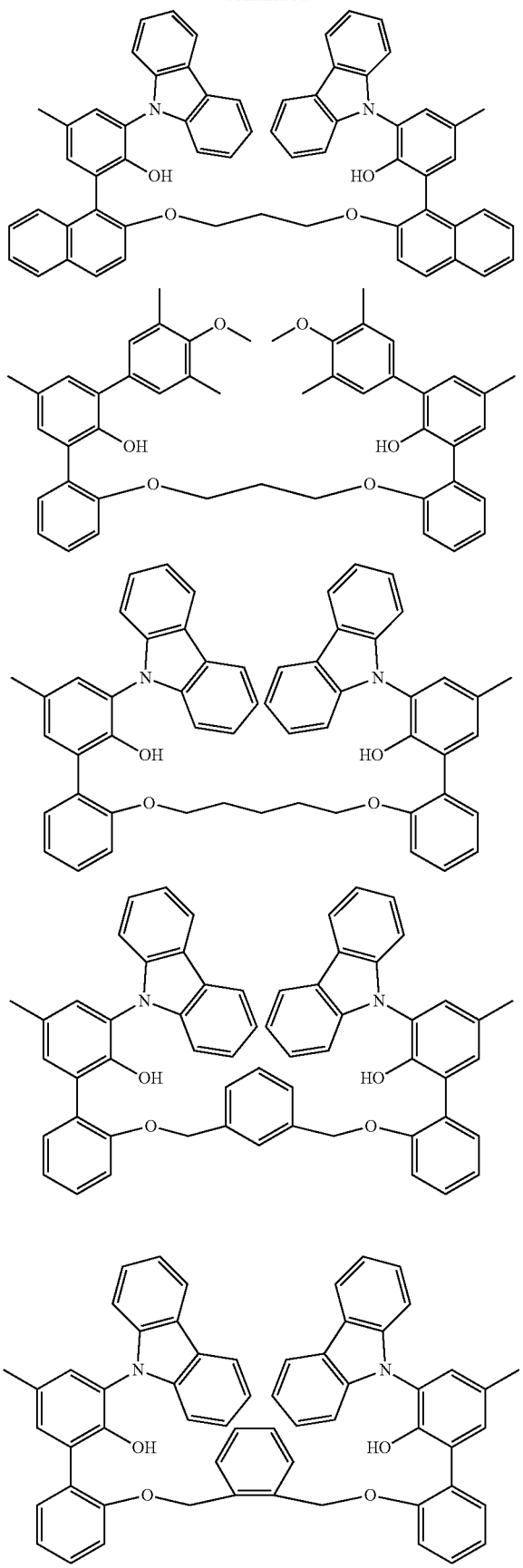
14
-continued
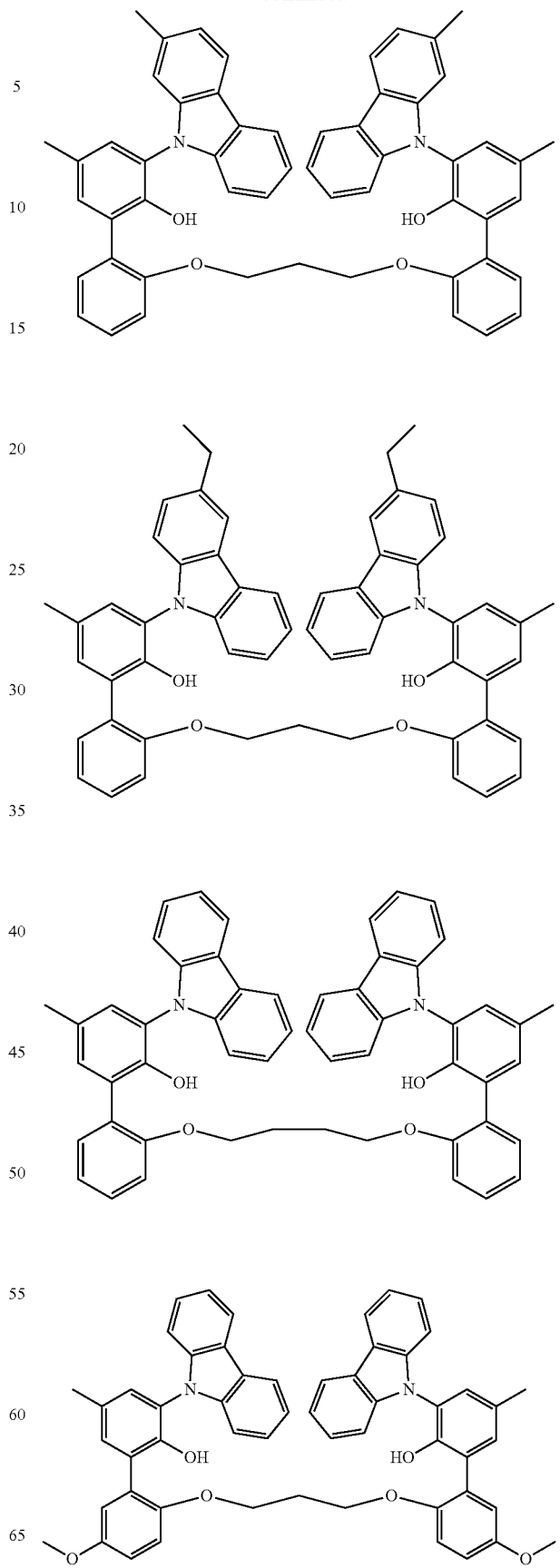

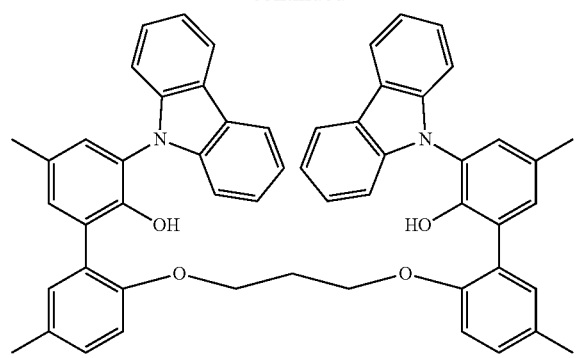
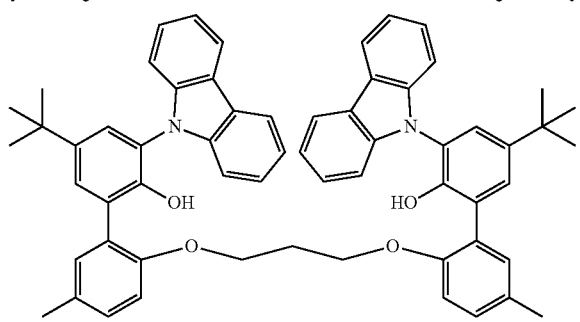
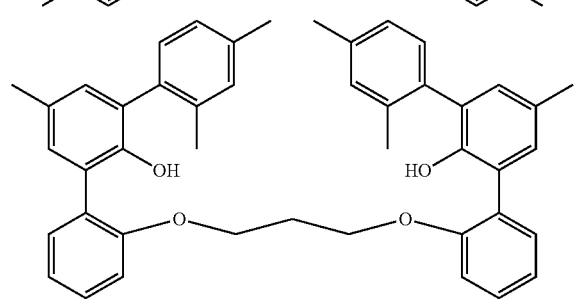
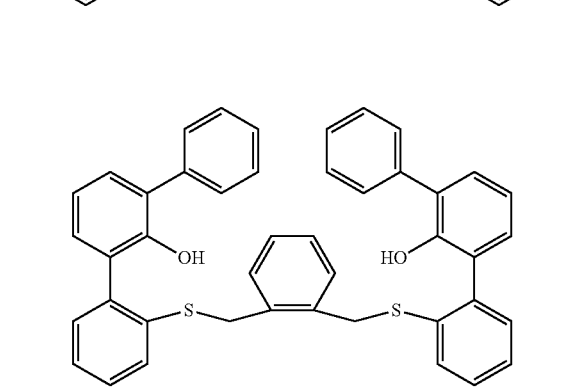
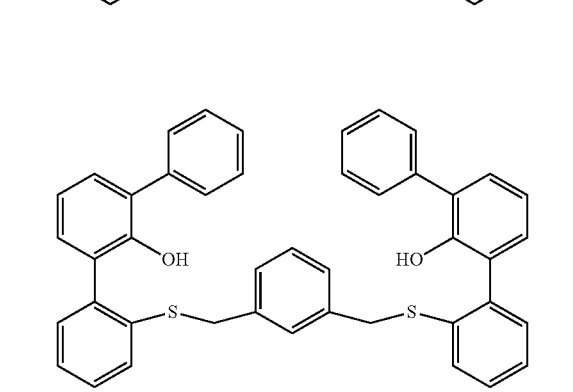
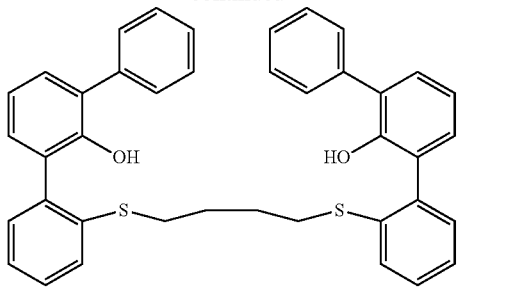
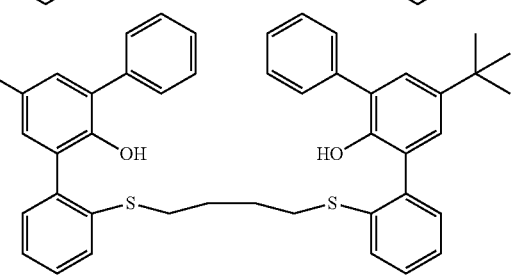
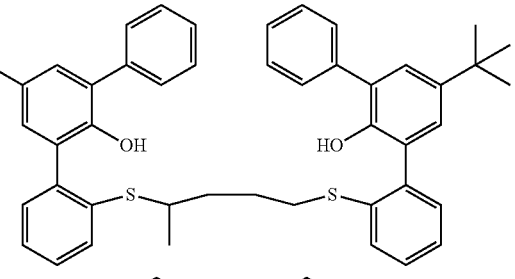
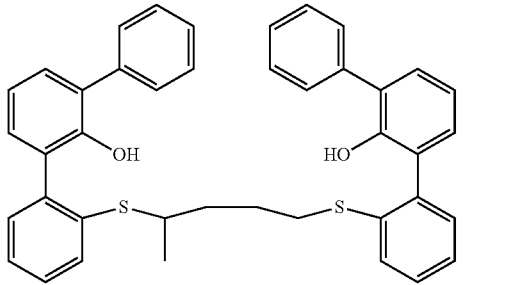
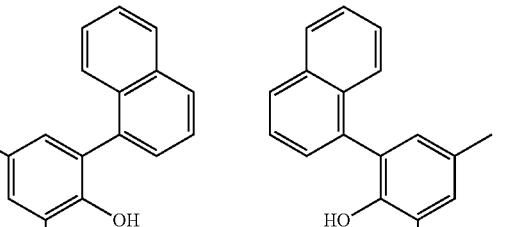
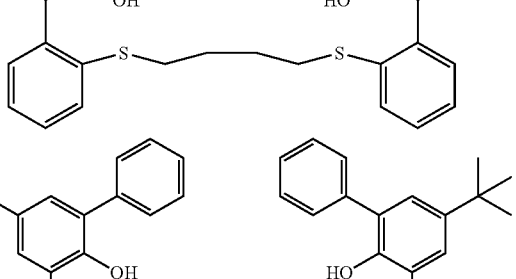
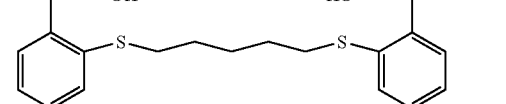

-continued
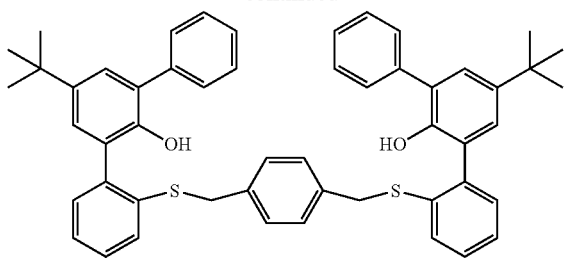
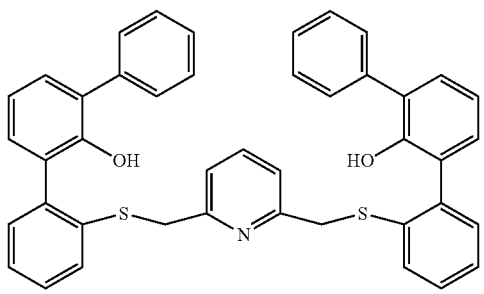
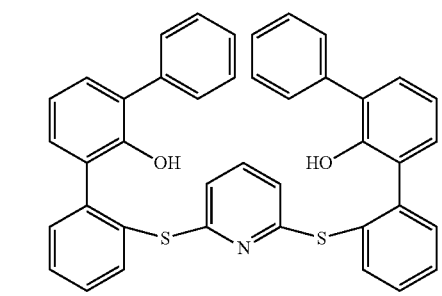
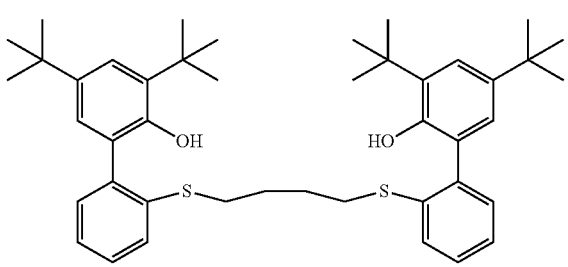
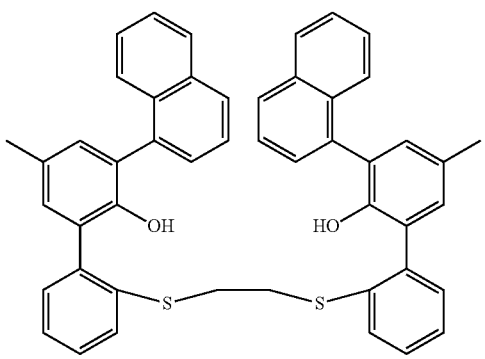
-continued
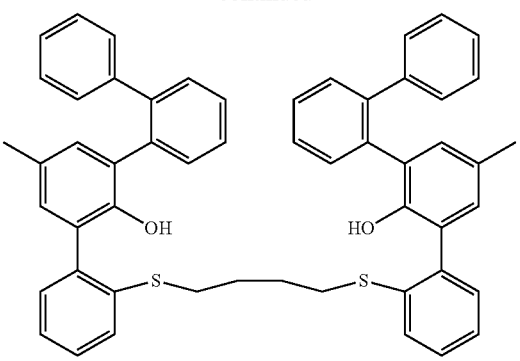
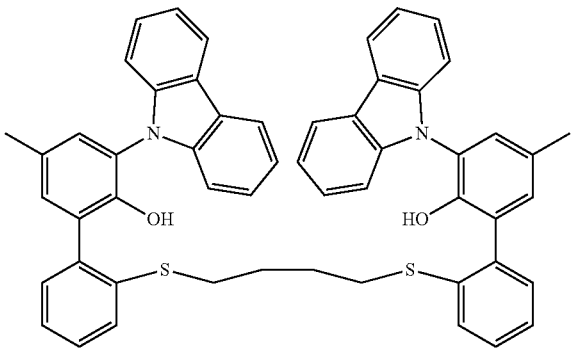
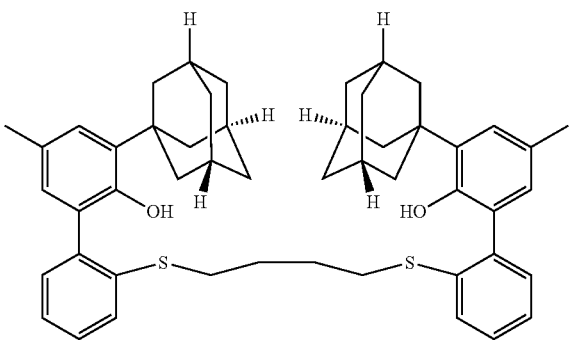
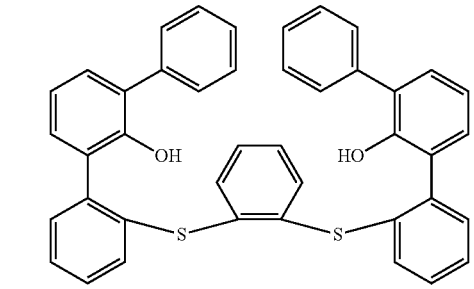
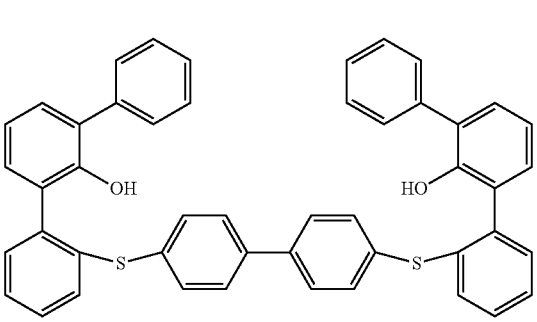

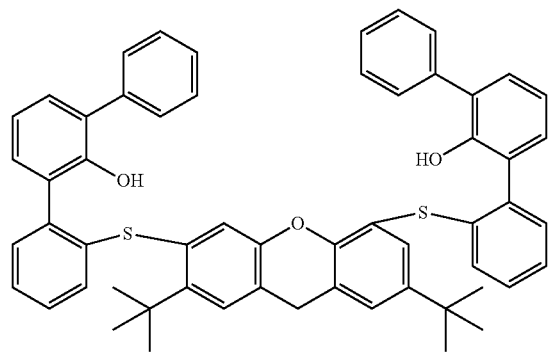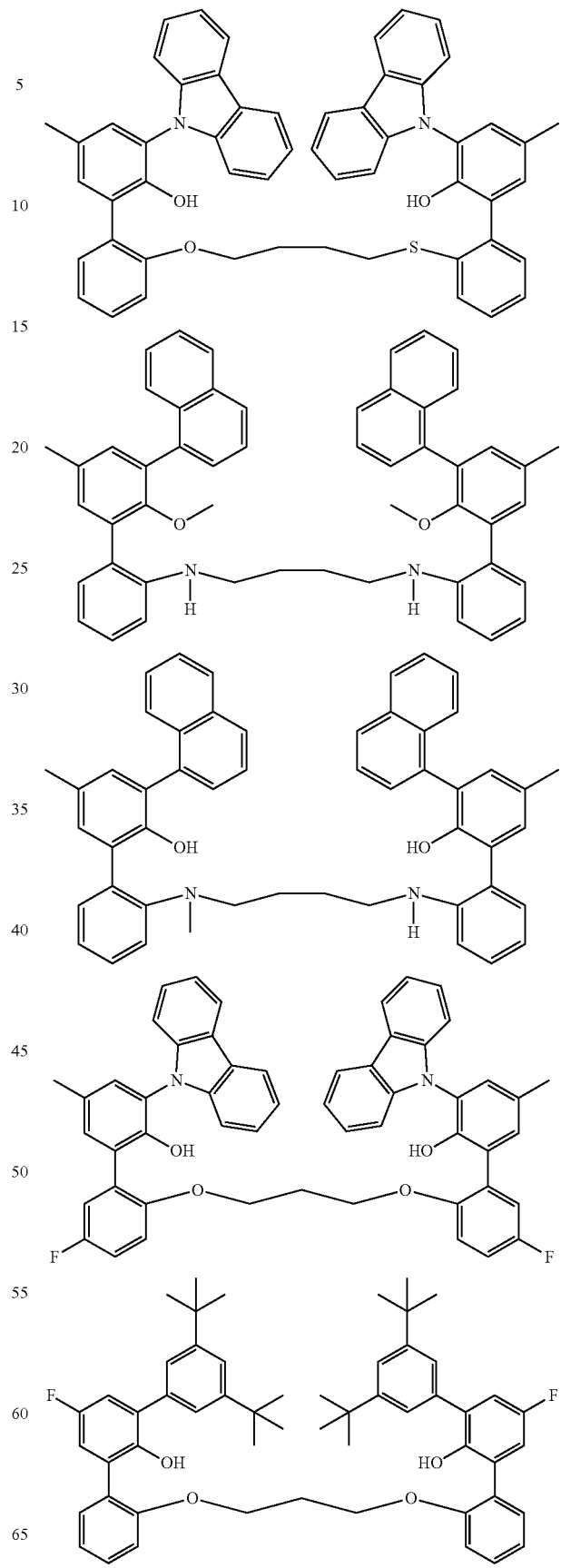

-continued

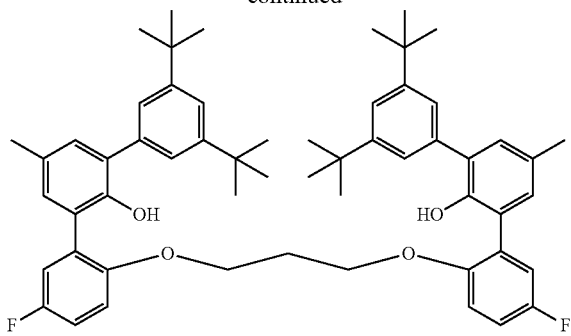

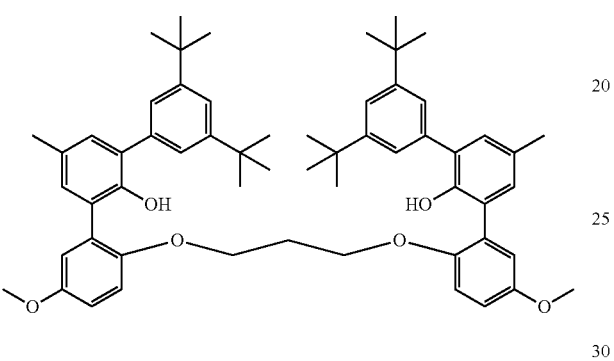

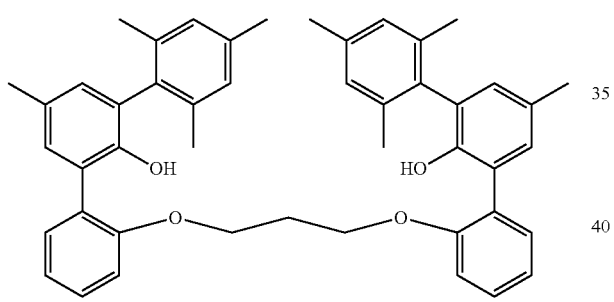

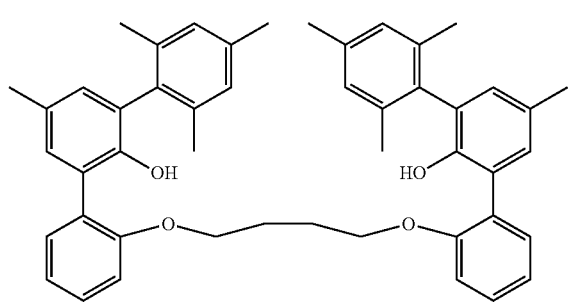

The ligands disclosed herein may be prepared by a variety of methods. In general the ligands may be prepared by employing di-ortho directed lithiations of the aromatic rings of bridged protected di-phenols and aryl coupling reactions. The methods may comprise Negishi coupling.

The following Schemes illustrate general methods for the preparation of the ligands. Scheme 1 illustrates di-ortho lithiation of a bridged protected di-phenol.

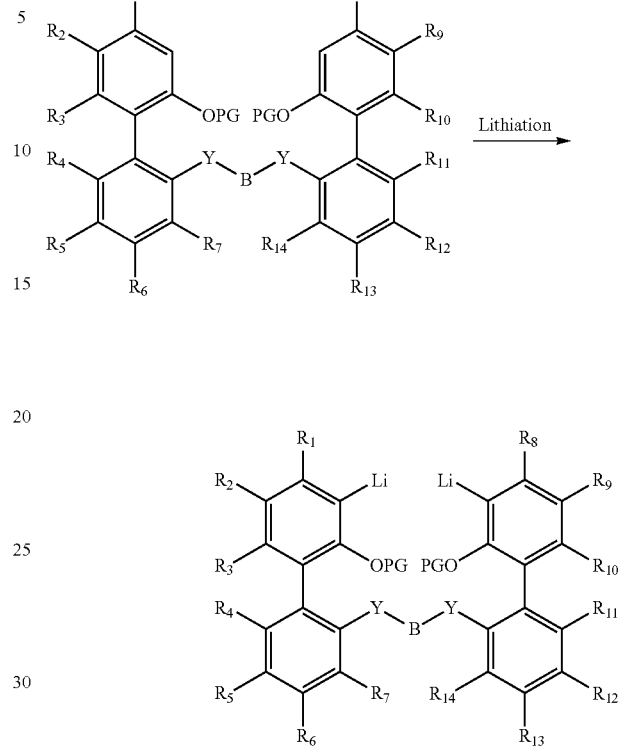

Scheme 2 illustrates a further di-ortho lithiation.

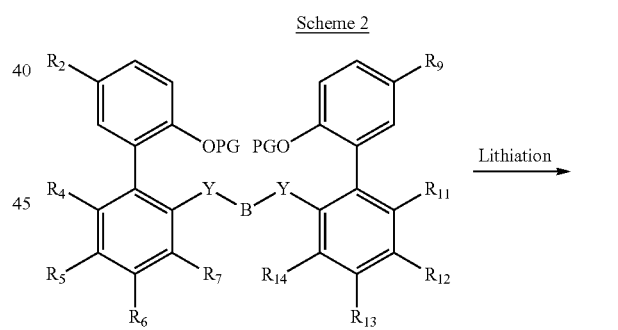

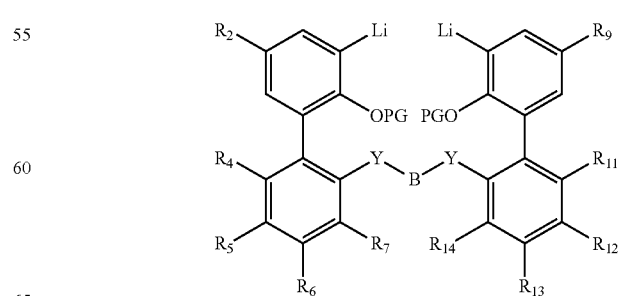

Scheme 3 illustrates acylation via Negishi coupling.

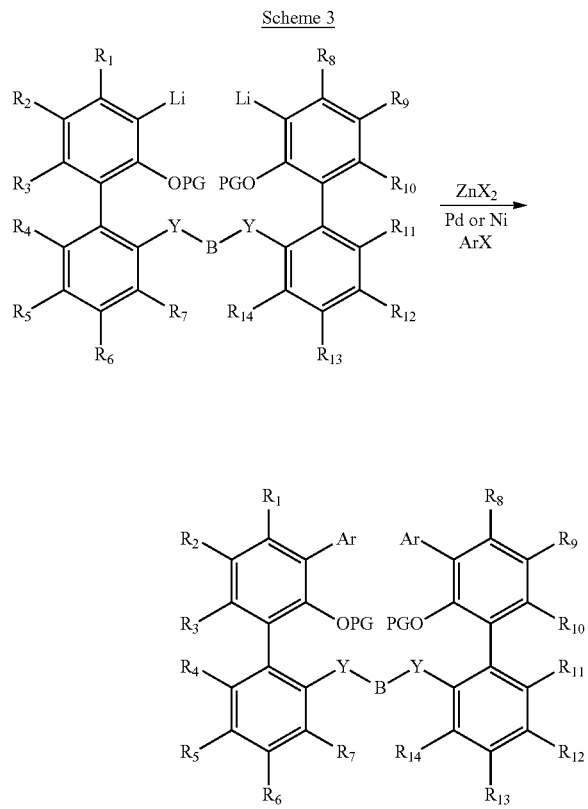

Scheme 4 illustrates acylation via Negishi coupling.

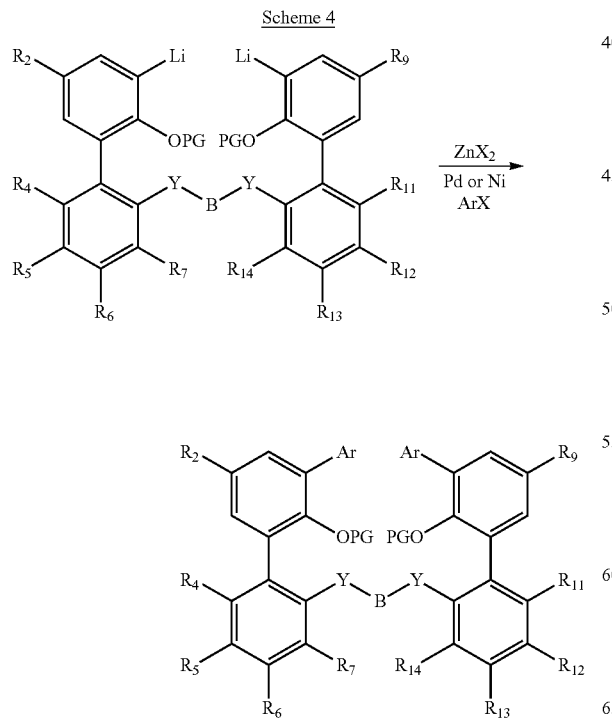

Scheme 5 illustrates deprotection.

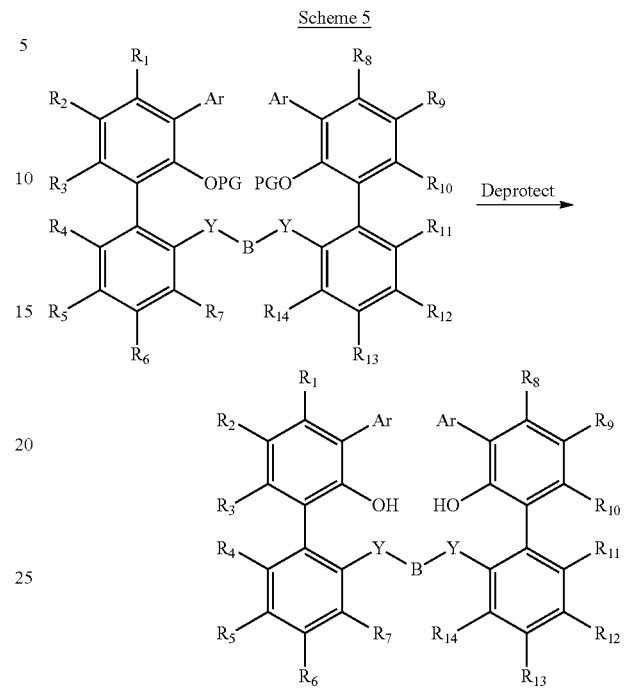

Scheme 6 illustrates deprotection.

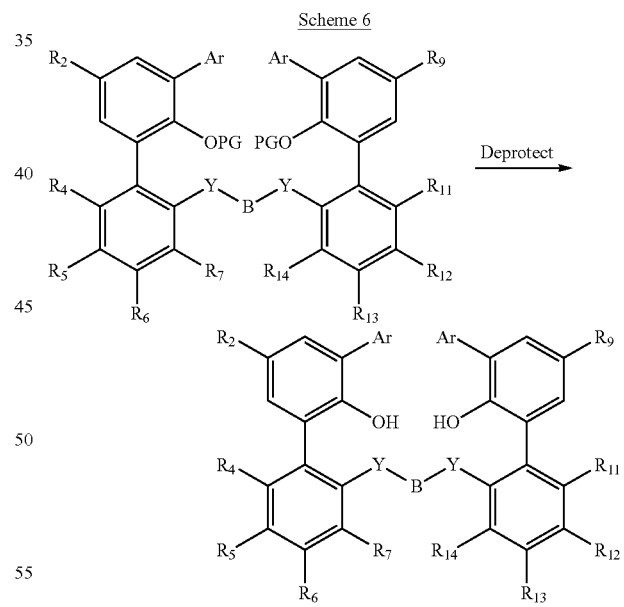

wherein in any one of the above methods each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; B is a bridging group having from one to 50 non-hydrogen atoms; Y and Y' are independently selected from O, S and NR$^a$ wherein R$^a$ is optionally substituted hydrocarbyl; Ar is optionally substituted aryl or heteroaryl; X is halide; PG is a protecting group.

In any one of the above methods each of R$^1$, R$^2$, R$^3$, R$^4$, R$^5$, R$^6$, R$^7$, R$^8$, R$^9$, R$^{10}$, R$^{11}$, R$^{12}$, R$^{13}$ and R$^{14}$ may be independently selected from the group consisting of hydride and optionally substituted aryl and hetroaryl.

In any of the above methods Y and Y' may be O.

In any of the above methods B may be selected from the group consisting of optionally substituted divalent alkyl, alkenyl, alkynyl, heteroalkyl, heteroalkenyl, heteroalkynyl, aryl, heteroaryl and silyl.

In any of the above methods lithiation may be performed with an alkyl or aryl lithium compound. For example. t-BuLi, lithium bis(trimethylsilyl)amide (LHMDS), lithium diisopropylamide, and lithium tetramethylpiperidide.

In any of the above methods the palladium catalyst may comprise a palladium phosphine compound, for example, bis(tri-tert-butylphosphine)palladium (Pd(PPh$_3$)$_4$), tetrakis (triphenylphosphine)palladium(0) (Pd(dppe)$_2$), bis[1,2-bis(diphenylphosphino)ethane]palladium(0) (Pd(dppf)), 1,1'-bis(diphenylphosphino)ferrocene palladium, and (2,2'-bis(diphenylphosphino)-1,1'-binaphthyl palladium (Pd (BINAP).

In any of the above methods the palladium catalyst may comprise a palladium compound and one or more phosphines. For example, tris(dibenzylideneacetone)dipalladium (0) (Pd$_2$(dba)$_3$) and Pd(OAc)$_2$ and one or more phosphine compounds.

In any of the above methods the zinc halide may be zinc (II) chloride.

In any one of the aforementioned embodiments deprotection may comprise treatment with acid. The acid may be any protic acid. Exemplary acids include hydrochloric acid or p-toluene sulphonic acid.

An advantage of the hereinbefore disclosed methods is the use of direct and selective di-ortho lithiation of the aromatic ring of a bridged protected di-phenol. This obviates the need to perform multiple halogenations of the phenol rings prior to lithiation, which is a feature of previously disclosed methods.

Figure 2:
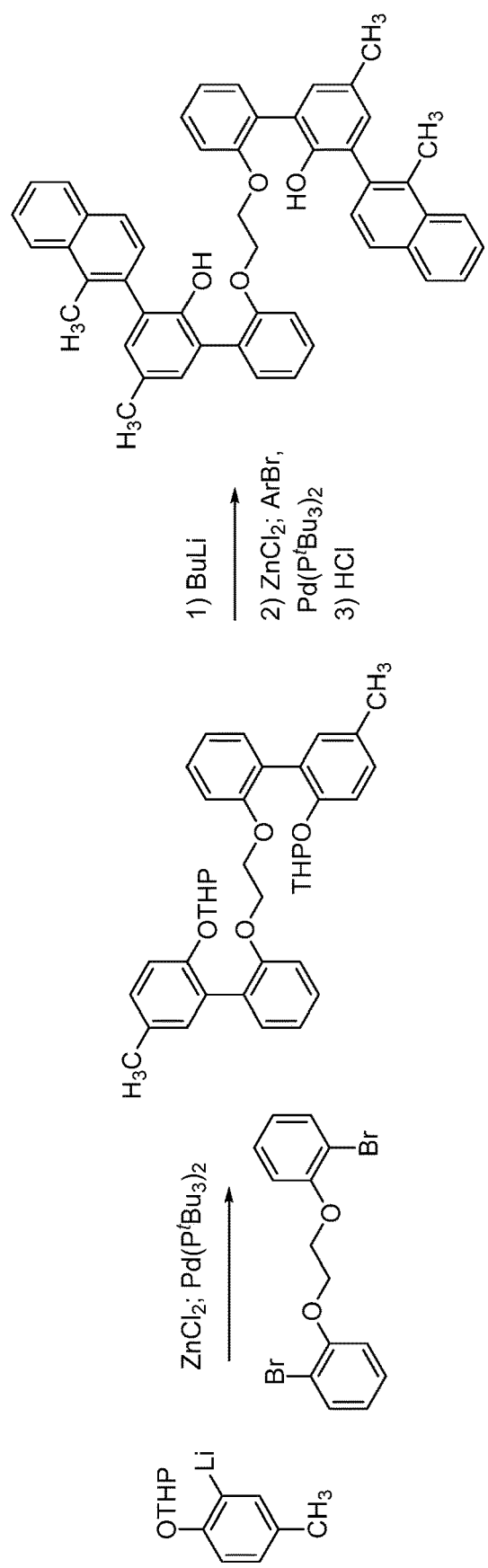
FIG. 2 depicts an exemplary reaction scheme in accordance with this disclosure.

In an illustrative embodiment and referring to the structures in FIG. 1 and the reaction scheme in FIG. 2, THP-protected cresol lithium salt was treated with zinc chloride. Subsequently, 1,2-bis(2-bromophenoxy)ethane and bis(tri-tert-butylphosphine)palladium were added and the mixture stirred at ambient temperature overnight. The resulting THP-protected bisphenol (1) was dissolved in THF and cooled to −20° C. n-Butyllithium was added and the solution allowed to warm to ambient temperature. A precipitate formed and the dilithium salt isolated. To the dilithium salt suspended in THF was added zinc dichloride followed by bromo-methyl naphthalene and bis(tri-tert-butylphosphine)palladium and the reaction stirred at ambient temperature overnight. This product was deprotected by dissolving it in THF/MeOH with a catalytic amount of HCl to yield ligand (2).

Figure 3:
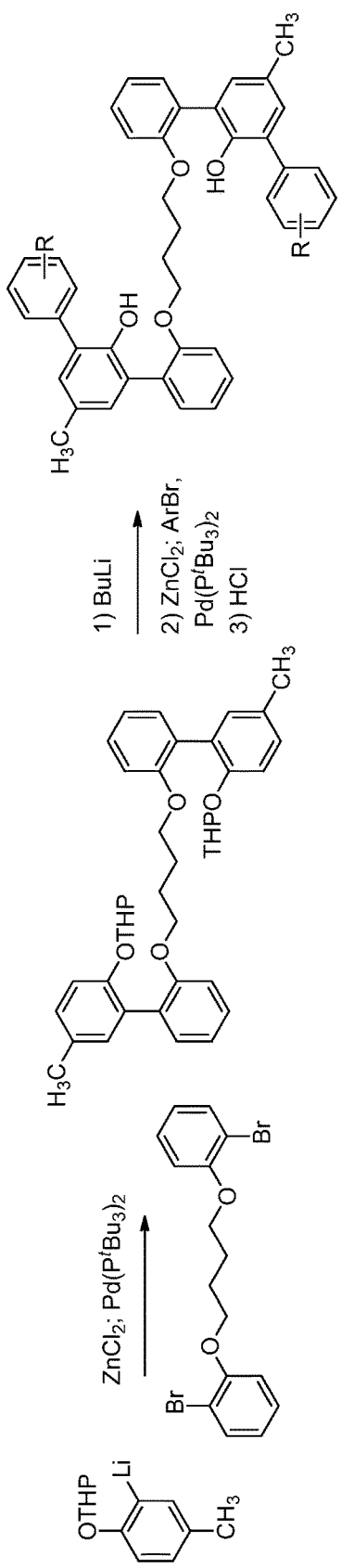
FIG. 3 depicts an exemplary reaction scheme in accordance with this disclosure.

FIG. 3 illustrates a similar reaction scheme for a higher homologue ligand.

Transition Metal Ligand Compounds

The transition metal ligand compounds may be prepared by any suitable synthesis method and the method of synthesis is not critical to the present disclosure. One useful method of preparing the transition metal ligand compounds of the present disclosure is by reacting a suitable metal compound, for example one having a displaceable anionic ligand, with the bridged bi-aromatic ligands of this disclosure. Non-limiting examples of suitable metal compounds include organometallics, metal halides, sulfonates, carboxylates, phosphates, organoborates (including fluoro-containing and other subclasses), acetonacetonates, sulfides, sulfates, tetrafluoroborates, nitrates, perchlorates, phenoxides, alkoxides, silicates, arsenates, borohydrides, naphthenates, cyclooctadienes, diene conjugated complexes, thiocyanates, cyanates, and the metal cyanides. The metal compound may be an organometallic or metal halide. The metal compound may be an organometallic.

The metal of the organometallic compound may be selected from Groups 1 to 16, or a transition metal selected from Groups 3 to 13 elements and Lanthanide series elements. The metal may be selected from Groups 3 to 7 elements. The metal may be a Group 4 metal, titanium, zirconium or hafnium.

The metal compound can, for example, be a metal hydrocarbyl such as: a metal alkyl, a metal aryl, a metal arylalkyl; a metal silylalkyl; a metal diene, a metal amide; or a metal phosphide. The metal compound may be a zirconium or hafnium hydrocarbyl.

An exemplary reaction is illustrated below.

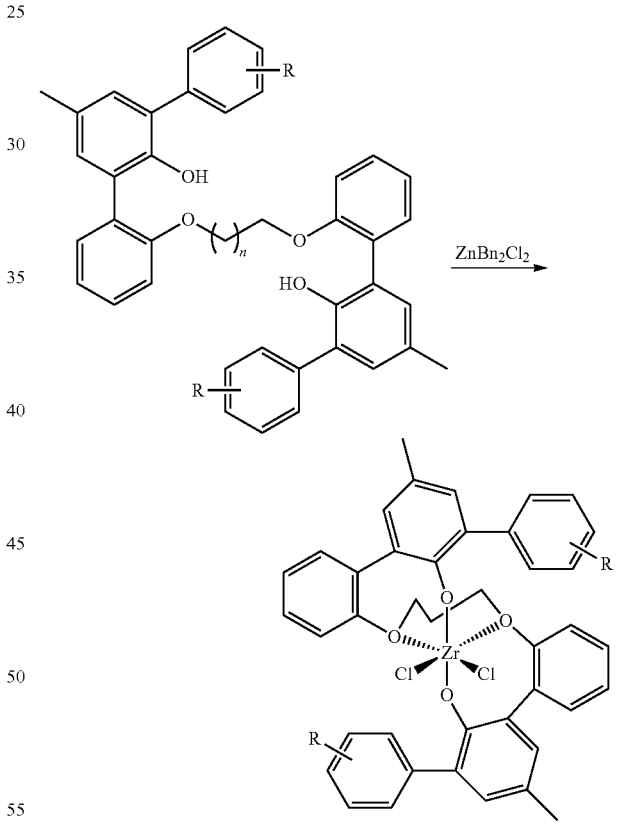

Examples of useful metal compounds include:
(i) tetramethylzirconium, tetraethylzirconium, zirconiumdichloride ($\eta^4$-1,4-diphenyl-1,3-butadiene), bis (triethylphosphine) and zirconiumdichloride ($\eta^4$-1,4-diphenyl-1,3-butadiene) bis(tri-n-propylphosphine), tetrakis[trimethylsilylmethyl]zirconium, tetrakis[dimethylamino] zirconium, dichlorodibenzylzirconium(diethyletherate), chlorotribenzylzirconium, trichlorobenzylzirconium, bis[dimethylamino]bis[benzyl]zirconium, and tetrabenzylzirconium;

(ii) tetramethyltitanium, tetraethyltitanium, titaniumdichloride ($\eta^4$-1,4-diphenyl-1,3-butadiene), bis (triethylphosphine) and titaniumdichloride ($\eta^4$-1,4-diphenyl-1,3-butadiene) bis (tri-n-propylphosphine), tetrakis[trimethylsilylmethyl]titanium, tetrakis[dimethylamino]titanium, dichlorodibenzyltitanium, chlorotribenzyltitanium, trichlorobenzyltitanium, bis[dimethylamino]bis[benzyl]titanium, and tetrabenzyltitanium; and (iii) tetramethylhafnium, tetraethylhafnium, hafniumdichloride ($\eta^4$-1,4-diphenyl-1,3-butadiene), bis (triethylphosphine) and hafniumdichloride ($\eta^4$-1,4-diphenyl-1,3-butadiene) bis (tri-n-propylphosphine), tetrakis[trimethylsilylmethyl]hafnium, tetrakis[dimethylamino]hafnium, dichlorodibenzylhafnium(diethyletherate), chlorotribenzylhafnium, trichlorobenzylhafnium, bis[dimethylamino]bis[benzyl]hafnium, and tetrabenzylhafnium.

EXAMPLES

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the following examples are put forth so as to provide those skilled in the art with a complete disclosure and description of how to make and use the disclosed compositions, and are not intended to limit the scope of the disclosure.

All reagents were purchased from commercial vendors and used as received unless otherwise noted. Solvents were sparged with $N_2$ and dried over 3 Å molecular sieves. Analytical thin-layer chromatography (TLC) was performed on Selecto Plates (200 µm) precoated with a fluorescent indicator. Visualization was effected using ultraviolet light (254 nm). Flash column chromatography was carried out with Sigma Aldrich Silica gel 60 Å (70-230 Mesh) using solvent systems specified. NMR spectra were recorded on a Bruker 400 or 500 NMR with chemical shifts referenced to residual solvent peaks.

1,2-bis ((5'-methyl-2'-((tetrahydro-2H-pyran-2-yl)oxy)-[1,1'-biphenyl]-2-yl)oxy)ethane (1)

THP-protected cresol lithium salt (4.88 g, 18.1 mmol) was suspended in 60 mL THF. Dry zinc chloride (3.04, 22.3 mmol) was added, turning the solution clear. After 20 min, 1,2-bis(2-bromophenoxy)ethane and bis(tri-tert-butylphosphine)palladium (250 mg, 0.55 mmol) were added and the orange solution stirred at ambient temperature overnight. Water and toluene were added to the reaction and the organic layer separated, washed with 2 portions of water, dried ($MgSO_4$), filtered, and concentrated.

2',2'''-(ethane-1,2-diylbis(oxy))bis(5-methyl-3-(2-methylnaphthalen-1-yl)-[1,1'-biphenyl]-2-ol) (2)

The above THP-protected bisphenol (1) (3.08 g, 5.1 mmol) was dissolved in 20 mL of THF and cooled to −20° C. n-Butyllithium (4.25 mL, 2.62 M in hexanes) was added and the solution allowed to warm to ambient temperature. A precipitate formed after 30 min and then the reaction was stirred for an additional 2.5 h. The solid was collected by filtration and washed with THF giving 2.5 g of dilithium salt. To the dilithium salt (1.24 g, 1.66 mmol) suspended in 20 mL of THF was added zinc dichloride (270 mg, 1.98 mmol). After 20 min, bromo-methyl naphthalene (740 mg, 3.35 mmol) and bis(tri-tert-butylphosphine)palladium (33 mg, 0.06 mmol) were added and the reaction stirred at ambient temperature overnight. Toluene was added, the THF removed under vacuum, and the solution washed with 3 portions of water. It was then dried ($MgSO_4$), filtered, and concentrated to a yellow oil. This oil was deprotected by dissolving it in 30 mL of THF/MeOH (1:2) with a catalytic amount of HCl. The reaction was allowed to stir overnight, then concentrated and redissolved in toluene. After drying over $Na_2CO_3$ and $MgSO_4$ and removal of toluene, the product was obtained as a white solid in 25% yield.

Zr Complex (3)

$ZrBn_2Cl_2(Et_2O)$ (255 mg, 0.61 mmol) was dissolved in about 5 mL of toluene and combined with a toluene solution of the ligand (2) (450 mg, 0.64 mmol). The solution was heated at 85° C. for about 2 h as a grey precipitate formed. The solid was collected by filtration and washed with toluene and pentane. $^1$H NMR shows the product as 2 major isomers.

2,2''''-(ethane-1,2-diylbis(oxy))bis(5'-methyl-[1,1':3', 1'':4'',1'''-quaterphenyl]-2'-ol) (4)

To the dilithium salt of the above THP-protected bisphenol (1) (1.19 g, 1.59 mmol) suspended in 20 mL of THF was added zinc dichloride (440 mg, 3.22 mmol). After stirring for 15 min, 4-bromobiphenyl (750 mg, 3.22 mmol) and bis(tri-tert-butylphosphine)palladium (53 mg, 0.10 mmol) were added and the reaction heated at 65° C. for 30 min. After cooling, toluene and water were added to the reaction and the mixture washed with water, dried ($MgSO_4$), filtered and concentrated. The oil was redissolved in THF/MeOH (1:2) and deprotected with catalytic HCl as described above.

Zr Complex (5)

$ZrBn_2Cl_2(Et_2O)$ (520 mg, 1.24 mmol) was dissolved in about 15 mL of toluene and combined with a toluene solution of the ligand (4) (912 mg, 1.25 mmol). The solution was heated at 85° C. for about 2 h, forming a white precipitate. The solid was collected by filtration and washed with pentane, giving 1.01 g of product.

1,4-bis((5'-methyl-2'-((tetrahydro-2H-pyran-2-yl)oxy)-[1,1'-biphenyl]-2-yl)oxy)butane (6)

Prepared following the Negishi coupling procedure described above. A lithium salt of THP protected cresol (9.7 g, 34 mmol) and $ZnCl_2$ (6.08 g, 42 mmol) were reacted for 20 min before adding bis(tri-tert-butylphosphine)palladium (360 mg, 0.68 mmol) and 1,4-bis(2-bromophenoxy)butane (7.24 g, 17 mmol), then stirred at ambient temperature overnight. $^1$H NMR (400 MHz, $CDCl_3$) δ 1.39-1.81 (m, 10H), 2.28 (s, 6H), 3.47 (m, 2H), 3.71 (m, 2H), 3.83 (m, 4H), 5.21 (m, 2H), 6.85 (d, J=8.0 Hz, 2H), 6.96 (m, 2H), 7.05 (m, 6H), 7.25 (m, 4H).

2',2'''-(butane-1,4-diylbis(oxy))bis(5-methyl-3-(2-methylnaphthalen-1-yl)-[1,1'-biphenyl]-2-ol) (7)

The above protected bisphenol (6) (12.9 g, 20.7 mmol) was dilithiated with n-butyllithium (17.4 mL, 2.5 mmol in hexanes) and coupled as previously described. The dilithium salt (3 g, 4.7 mmol) and zinc dichloride (770 mg, 5.6 mmol) were dissolved in THF, then heated overnight with bromomethylnaphthalene (1.47 mL, 9.5 mmol) and bis(tri-tert-butylphosphine)palladium (48 mg, 0.09 mmol). The resulting product was deprotected with a solution of p-TSA (approx. 100 mg) in THF/EtOH (1:1). $^1$H NMR (400 MHz, CDCl$_3$) δ 1.66 (br s, 4H), 2.23 (s, 4H), 2.26 (s, 2H), 2.35 (s, 6H), 3.79 (br s, 2H), 6.85 (d, J=8.0 Hz, 2H), 6.94 (m, 2H), 7.14 (m, 4H), 7.39 (m, 12H), 7.80 (m, 4H).

Zr Complex (8)

Ligand (7) (140 mg, 190 mmol) was dissolved in 5 mL of toluene and combined with a 5 mL toluene solution of ZrBn$_2$Cl$_2$(Et$_2$O) (75 mg, 190 mmol). The solution was heated at 80° C. for 2 h, then concentrated to a solid which was recrystallized in toluene and hexane.

2,2''''-(butane-1,4-diylbis(oxy))bis(5'-methyl-[1,1':3', 1'':4'',1'''-quaterphenyl]-2'-ol) (9)

The above protected bisphenol (6) (12.9 g, 20.7 mmol) was dilithiated with n-butyllithium (17.4 mL, 2.5 mmol in hexanes) and coupled as previously described. The dilithium salt (3 g, 4.7 mmol) and zinc dichloride (770 mg, 5.6 mmol) were dissolved in THF, then heated overnight with bromobiphenyl (2.2 g, 9.5 mmol) and bis(tri-tert-butylphosphine) palladium (48 mg, 0.09 mmol). The resulting product was deprotected with a solution of p-TSA (approx. 100 mg) in THF/EtOH (1:1). $^1$H NMR (400 MHz, CDCl$_3$) δ 1.81 (m, 4H), 2.33 (s, 6H), 3.96 (m, 4H), 6.91 (d, J=8.0 Hz, 2H), 7.03 (d, J=2.0 Hz, 2H), 7.11 (t, J=7.2 Hz, 2H), 7.17 (d, J=2.0 Hz, 2H), 7.37 (m, 6H), 7.45 (m, 6H), 7.56 (m, 2H), 7.63 (m, 6H).

Zr Complex (10)

Ligand (9) (122 mg, 160 mmol) was dissolved in 5 mL of toluene and combined with a 5 mL toluene solution of ZrBn$_2$Cl$_2$(Et$_2$O) (63 mg, 160 mmol). The solution was heated at 80° C. for 2 h, then concentrated to a solid which was recrystallized in toluene and hexane. Washing the pale yellow powder gave the product in 83% yield. NMR (400 MHz, CD$_2$Cl$_2$) δ 1.26 (m, 4H), 2.38 (s, 6H), 3.87 (m, 2H), 4.44 (m, 2H), 5.45 (m, 2H), 6.80 (m, 2H), 7.12 (m, 4H), 7.37 (m, 10H), 7.82 (m, 7H), 7.93 (m, 4H).

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited are herein fully incorporated by reference for all jurisdictions in which such incorporation is permitted and to the extent such disclosure is consistent with the description of the present disclosure.

What is claimed is:

1. A method for preparing a bridged bi-aromatic phenol ligand of formula (I) comprising:
deprotecting a protected bi-aromatic phenol of formula (IV):

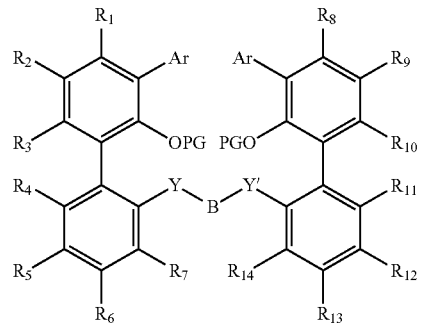

to yield the bridged bi-aromatic phenol ligand of formula (I):

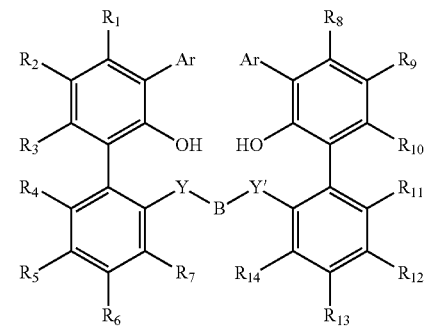

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; B is a bridging group having from one to 50 non-hydrogen atoms; Y and Y' are independently selected from O, S, NR$^a$ and PR$^a$ wherein R$^a$ is optionally substituted hydrocarbyl; Ar is optionally substituted aryl or heteroaryl and PG is a protecting group.

2. A method according to claim 1 comprising at least one step of aryl coupling.

3. A method according to claim 2 wherein the aryl coupling comprises at least one step of Negishi coupling.

4. A method according to claim 1 comprising the steps of:
a) treating a protected bi-aromatic phenol of formula (II) with a lithiating agent to yield a dilithio protected bi-aromatic phenol of formula (III);

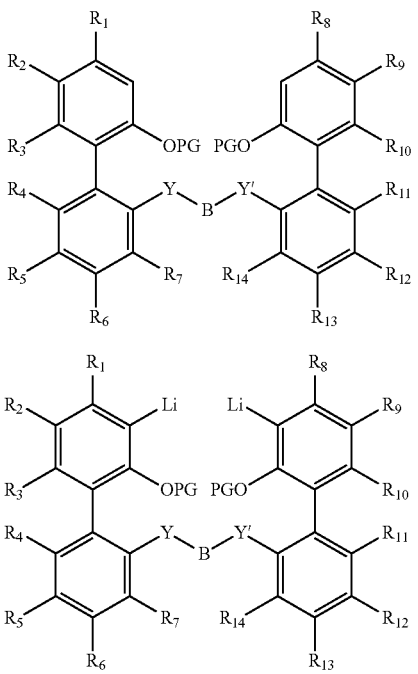

(II)

(III)

b) treating the dilithio protected bi-aromatic phenol of formula (III) with a zinc compound and a compound of formula ArX in the presence of a palladium or nickel catalyst, to yield the protected bi-aromatic phenol of formula (IV);

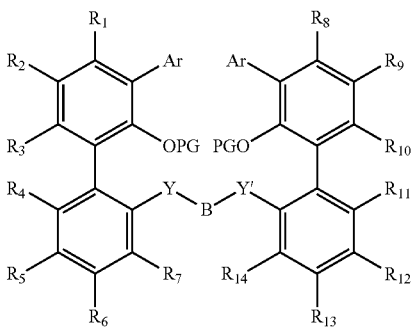

(IV)

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; B is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or heteroaryl; X is halide; PG is a protecting group.

5. A method according to claim 4 comprising the steps of:
a) treating the dilithio protected bi-aromatic phenol of formula (III) with a zinc halide to yield the zinc halide salt of a protected bi-aromatic phenol of formula (V); and

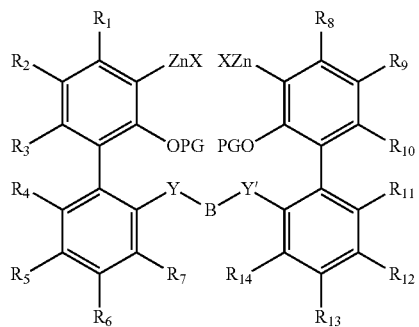

(V)

b) treating the zinc halide salt of the protected bi-aromatic phenol of formula (V) with a compound of formula ArX in the presence of a palladium or nickel catalyst to yield the compound of formula (IV).

6. A method according to claim 1, wherein the bridging group B is selected from the group consisting of optionally substituted divalent hydrocarbyl and divalent heteroatom containing hydrocarbyl.

7. A method according to claim 1, wherein B is selected from the group consisting of optionally substituted divalent alkyl, alkenyl, alkynyl, heteroalkyl, heteroalkenyl, heteroalkynyl, aryl, heteroaryl and silyl.

8. A method according to claim 1, wherein B is represented by the general formula $-(QR^{15}_{2-z''})_{z'}-$ wherein each Q is either carbon or silicon and each $R^{15}$ may be the same or different from the others such that each $R^{15}$ is selected from the group consisting of hydrogen and optionally substituted hydrocarbyl and heteroatom containing hydrocarbyl, and optionally two or more $R^{15}$ groups may be joined into a ring structure having from 3 to 50 atoms in the ring structure not counting hydrogen atoms; z' is an integer from 1 to 10; and z'' is 0, 1 or 2.

9. A method according to claim 1 wherein B comprises optionally substituted divalent alkyl.

10. A method according to claim 1 wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, and optionally substituted alkyl and aryl.

11. A method according to claim 1 wherein Ar is independently selected from the group consisting of optionally substituted phenyl, naphthyl, biphenyl, anthracenyl, and phenanthrenyl.

12. A method according to claim 1 wherein Ar is independently selected from the group consisting of thiophene, pyridine, isoxazole, pyrazole, pyrrole, furan or benzo-fused analogues of these rings.

13. A method according to claim 3 wherein PG is selected from methyl, benzyl, substituted benzyl, alkoxymethyl, tetrahydropyranyl, silyl, and allyl.

14. A method according to claim 1 wherein lithiation is performed with an alkyl or aryl lithium compound.

15. A method according to claim 1 wherein lithiation is performed with $^n$BuLi.

16. A method according to claim 4 wherein the zinc compound or the zinc halide comprises zinc (II) chloride.

17. A method according to claim 4 wherein the palladium or nickel catalyst comprises a palladium or nickel phosphine compound.

18. A method according to claim 17 wherein the palladium phosphine compound comprises bis(tri-tert-butylphosphine)palladium.

* * * * *